United States Patent
Rodefeld et al.

(10) Patent No.: US 6,465,678 B1
(45) Date of Patent: Oct. 15, 2002

(54) METHOD FOR PREPARING METHYL CARBAZATE

(75) Inventors: Lars Rodefeld, Leverkusen (DE); Horst Behre, Odenthal (DE); Alexander Klausener, Pulheim (DE); Robert Söllner, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/889,813

(22) PCT Filed: Jan. 17, 2000

(86) PCT No.: PCT/EP00/00310

§ 371 (c)(1),
(2), (4) Date: Jul. 20, 2001

(87) PCT Pub. No.: WO00/44708

PCT Pub. Date: Aug. 3, 2000

(30) Foreign Application Priority Data

Jan. 26, 1999 (DE) .......................... 199 02 960

(51) Int. Cl.⁷ ............................................. C07C 229/00
(52) U.S. Cl. ..................... 560/155; 560/157; 560/29; 564/37
(58) Field of Search ................ 560/157, 155, 560/29; 564/37

(56) References Cited

U.S. PATENT DOCUMENTS 4,496,761 A * 1/1985 Lange, Jr. ............... 564/37
4,596,884 A * 6/1986 Madding ................. 560/29

FOREIGN PATENT DOCUMENTS

| DE | 285800  | 2/1914  |
| DE | 3443820 | 6/1985  |
| EP | 103400  | 3/1984  |
| SU | 407888  | 12/1973 |

OTHER PUBLICATIONS

O. Diels, Ber.(month unavailably) 1914 pp. 2183–2195, Darstellung und neue Reaktionen der Hydrazin–monocarbonsaureester.

* Data Base WPI, Week 197438, Derwebt Oybkucatuib Ktdm, Kibdibrn GB; AN 1974–67396v, SP002133241 & SU 407 888 A (Biolog Medic Chem Inst), Apr. 25, 1974.

* cited by examiner

*Primary Examiner*—Alan L. Rotman
*Assistant Examiner*—Hector M Reys
(74) *Attorney, Agent, or Firm*—Joseph C. Gil; Diderico van Eyl

(57) ABSTRACT

Methyl carbazate which is particularly pure and has a particularly low tendency toward discoloration is obtained from hydrazine and dimethyl carbonate if the two reactants are metered simultaneously into an initially introduced first solvent at from −20 to +30° C., the solvent and low-boiling components are then distilled off under reduced pressure, and then either a second solvent is added to the crude methyl carbazate present and this solvent is distilled off under reduced pressure or an inert gas is passed through the crude methyl carbazate present.

21 Claims, No Drawings

METHOD FOR PREPARING METHYL CARBAZATE

The present invention relates to a particularly advantageous process for the preparation of methyl carbazate by reaction of hydrazine with dimethyl carbonate.

Methyl carbazate, which is also known as methyl hydrazinocarboxylate, is a versatile synthesis unit in organic chemistry which can serve, for example, for the transfer of hydrazine or as protective group for carbonyls (see, for example, Technical Information "Methyl carbazate" from Bayer AG 4.97 and the literature cited therein).

The synthesis of methyl carbazate from hydrazine hydrate and dimethyl carbonate is known (see O. Diels, Ber. 1915, 2183–2195). The general equation for this is shown in Equation (1)

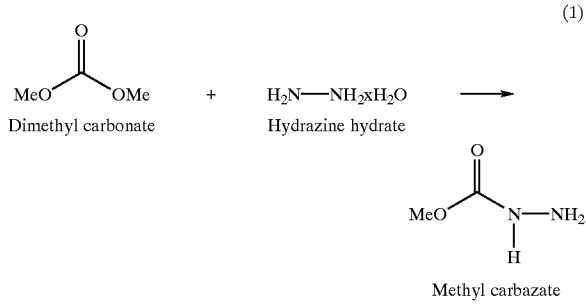

The process is carried out by combining the component one after the other and allowing the reaction to proceed with strong self-warming. Volatile constituents are then removed by distillation at 40 mbar and a bath temperature of 70° C.

DE 285 800 describes a very similar process for the preperation of methyl carbazate.

EP-A 0 103 400 describes a process in which the components are likewise combined one after the other, with dimethyl carbonate being employed in a slight excess. The reaction is carried out firstly at 50= C., later at 25° C. The distillative removal of water and methanol is carried out by distillation at 40 mbar.

Finally, DE 34 43 820 describes the preparation of methyl carbazate by initially introducing dimethyl carbonate and metering in hydrazine hydrate very quickly. During this addition, the reaction batch heats up very considerably. Volatile constituents are subsequently removed under reduced pressure.

If the synthesis of methyl carbazate is carried out in accordance with Diels, DE 285 800 or EP-A 0 103 400 on an industrial scale, products are always obtained which are contaminated by the undesired components of the formulae (I) and (II) up to about 3% by weight in each case.

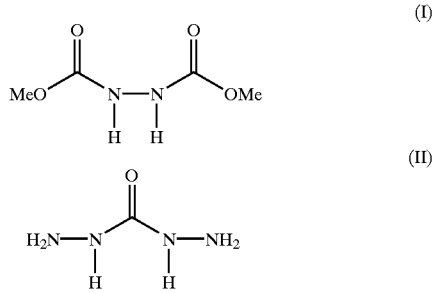

The method described in DE 34 43 820 results in products in which the undesired component of the formula (I) is enriched to a particularly great extent, for example in an amount of up to 4% by weight.

In addition, all the processes described above give methyl carbazate which turns a reddish colour after a few days. This is disadvantageous since methyl carbazate is used for the preparation of pharmaceutical products, where discoloured products are undesired.

In addition, methyl carbazate prepared by all the above processes contains a residual content of carcinogenic hydrazine of from about 100 to 500 ppm and a residual content of water of generally greater than 1% by weight. These residual contents cannot be reduced further in the distillative work-up used. Particularly problematic is the high residual content of hydrazine, which requires particular occupational-hygiene efforts on handling of such products.

There is therefore still the need for a process for the preparation of methyl carbazate in which a product is produced which has reduced contents of the undesired components of the formulae (I) and (II), of residual hydrazine and of residual water, and in addition has a lower tendency toward discoloration than the methyl carbazate prepared by known processes.

A process has now been found for the preparation of methyl carbazate from hydrazine and dimethyl carbonate which is characterized in that hydrazine and dimethyl carbonate are metered simultaneously into an initially introduced first solvent at from –20 to +30° C., the solvent and low-boiling components are then distilled off under reduced pressure, and either a second solvent is added to the crude methyl carbazate then present and the solvent is then distilled off under reduced pressure or a gas is passed through the crude methyl carbazate then present.

In the process according to the invention, hydrazine and dimethyl carbonate can be employed, for example, in a molar ratio of from 0.9 to 1.1:1. This ratio is preferably from 0.95 to 1.05:1, in particular 1:1.

The hydrazine can be employed, for example, in pure form or as a mixture with water. Such hydrazine/water mixtures may contain, for example, from 10 to 85% by weight of hydrazine. Particularly suitable is so-called hydrazine hydrate (containing 64% by weight of hydrazine).

Dimethyl carbonate can be employed in commercially available form.

The simultaneous metering of hydrazine and dimethyl carbonate is preferably carried out at from 0 to +20° C., in particular at from +5 to +10° C. The term "meter simultaneously" or "simultaneous metering" here is taken to mean not only the metering of precisely equal molar amounts of the two reactants per time unit, but also procedures in which one of the reactants is metered-in in a molar excess of not greater than 20%, preferably not greater than 5% (based on the other reactant) per time unit.

Suitable as the first solvent is, for example, water or an organic solvent, where the organic solvent can be, for example, straight-chain, branched or cyclic, unsubstituted or substituted aliphatic compounds having 1 to 20 carbon atoms or unsubstituted or substituted aromatic compounds having 6 to 10 carbon atoms. Suitable substituents for the aliphatic and aromatic compounds are, for example, halogen atoms, in particular chlorine atoms, hydroxyl groups, groups of the formula $X-R^3$, where X=oxygen or sulphur, and $R^3$=hydrogen, or straight-chain or branched $C_1-C_4$-alkyl, groups of the formula $COOR^3$, where $R^3$ is as defined above, and/or groups of the formula $NR^3R^4$, where $R^3$ is as defined above and $R^4$, independently of $R^3$, is as defined for $R^3$. It is also possible for a plurality of identical or different substituents of this type to be present, for example up to 4 units per molecule. Also suitable as the first solvent are hydrazine and dimethyl carbonate within the above-mentioned limitations for the molar excess of one of these reactants. It is also possible to employ any desired mixtures of said solvents. The first solvent is preferably straight-chain and branched aliphatic alcohols having 1 to 8 carbon atoms.

After completion of the metering, a post-reaction time may be observed, if desired, for example stirring of the reaction mixture at from +30 to +60° C., in particular at from +40 to +55° C., for from 30 to 300 minutes.

After completion of the metering and expiry of any post-reaction time observed, the solvent employed and the low-boiling components, essentially methanol formed, any water introduced with the hydrazine and any excesses of hydrazine or dimethyl carbonate are distilled off under reduced pressure. For example, the pressure here can be reduced to from 0.1 to 30 mbar. Pressure reductions to from 2 to 20 mbar, in particular from 5 to 10 mbar, are preferred.

This distillation can, if desired, be carried out in 2 stages, and the first solvent obtained in the distillation re-used, in full or in part, for the next batch.

In this way, the distillation residue obtained is a crude methyl carbazate. This is then purified further, it being possible to use 2 different methods.

Method A: A second solvent, which can be, for example, an organic solvent, as described above for the first solvent, can be added to the crude methyl carbazate. The second solvent is preferably unsubstituted and substituted aromatic compounds, such as benzene, toluene, xylene and chlorobenzene. The second solvent is then distilled off at pressures as described for the distillation of the first solvent.

Method B: A gas is passed through the crude methyl carbazate. Suitable gases are, for example, nitrogen, air, oxygen or noble gases. The crude methyl carbazate is advantageously held here at a temperature at which it is liquid and still does not have an excessively high vapour pressure, for example at from 75 to 120° C.

After performance of the process according to the invention, the residue obtained is a methyl carbazate which, compared with the methyl carbazate obtainable by the processes known hitherto, contains significantly less of the undesired components of the formulae (I) and (II), significantly less hydrazine and significantly less water and in addition has a significantly lower tendency toward discoloration. It is extremely surprising that these advantages are achieved, since the change in the metering of the reactants, the reduction in the initial reaction temperature and the further purification based exclusively on physical methods, which has in principle already also been carried out, did not give rise to expectations of this.

EXAMPLES

Unless otherwise stated, percentages are per cent by weight.

Example 1

2800 g of methanol were initially introduced and cooled to +5° C. 7560 g of dimethyl carbonate and 4200 g of hydrazine hydrate were then metered in precisely simultaneously over the course of 10 hours, during which the temperature was held at between +5 and +10° C. The mixture was then warmed to 50° C., and this temperature was maintained for one hour. 5124 g of a mixture essentially comprising methanol and dimethyl carbonate were subsequently distilled off first at this temperature and reducing pressure down to 140 bar, and then 2115 g of a mixture comprising methanol, water and residual hydrazine was distilled off at 80° C. and reducing pressure down to 8 mbar. The apparatus was then aerated with nitrogen, and 1823 g of toluene were added, which was then distilled off at 80° C. and reducing pressure down to 8 mbar in the form of 2561 g of a mixture comprising toluene, water, hydrazine and methyl carbazate. The sublimate precipitating in the distillation bend was melted off at 75° C. and allowed to run back into the reactor.

6583 g of methyl carbazate having a purity of 98.2% were obtained in the reaction vessel. The undesired component of the formula (I) was present in an amount of 1.2%, the undesired component of the formula (II) in an amount of 0.5%. The product contained 0.1% of water and 55 ppm of hydrazine.

Example 2

A sample of the methyl carbazate prepared in accordance with Example 1 and a sample of methyl carbazate prepared in accordance with DE 34 43 820 were analysed with respect to the discoloration occurred after a storage time of 1 month at +20° C. and in the dark. Degrees of transmission and Hazen colour numbers in a 5% strength aqueous solution were determined in accordance with DIN 55945. Results can be seen from the following table.

TABLE

| | Degrees of transmission | | | Hazen |
|---|---|---|---|---|
| | $T_x$ | $T_y$ | $T_z$ | number |
| Methyl carbazate obtained in accordance with Example 1 | 99.6 | 99.3 | 98.3 | 5 |
| Methyl carbazate obtained in accordance with DE 34 43 820 | 79.1 | 71.0 | 58.6 | 180 |

What is claimed is:

1. A process for preparing a methyl carbazate from hydrazine and dimethyl carbonate comprising:

(A) simultaneously metering hydrazine and dimethyl carbonate into an initially introduced first solvent at a temperature ranging from −20 to +30° C., (B) distilling off the solvent and low-boiling components under reduced pressure, and (C) adding a second solvent to crude methyl carbazate present and distilling off the second solvent under reduced pressure.

2. The process according to claim 1, wherein the hydrazine and the dimethyl carbonate are present at a molar ratio ranging from 0.9 to 1.1:1.

3. The process according to claim 1, wherein the first solvent is water or an organic solvent selected from the group consisting of a straight-chain compound having from 1 to 20 carbon atoms, a branched compound having from 1 to 20 carbon atoms, a cyclic compound having from 1 to 20 carbon atoms, an unsubstituted compound having from 1 to 20 carbon atoms, a substituted aliphatic compound having from 1 to 20 carbon atoms, an unsubstituted aromatic compound having from 6 to 10 carbon atoms, a substituted aromatic compound having from 6 to 10 carbon atoms, and mixtures thereof.

4. The process of claim 3, wherein the first solvent is selected from the group consisting of hydrazine, dimethyl carbonate, and mixtures thereof, wherein the hydrazine or the dimethyl carbonate is metered in at a molar excess that is not more than 20%, based on the other reactant, per time unit.

5. The process according to claim 1, wherein the first solvent is a straight-chain aliphatic alcohol having 1 to 8 carbon atoms or a branched aliphatic alcohol having 1 to 8 carbon atoms.

6. The process according to claim 1, wherein the hydrazine and the dimethyl carbonate are simultaneously metered so the hydrazine or the dimethyl carbonate is metered in at a molar excess of not greater than 20%, based on the other reactant, per time unit.

7. The process according to claim 1, wherein the process further comprises a post-reaction time period in which stirring is carried out at a temperature ranging from +30 to +60° C. from 30 to 300 minutes after the metering.

8. The process according to claim 1 wherein the second solvent is an organic solvent selected from the group consisting of a straight-chain compound having from 1 to 20 carbon atoms, a branched compound having from 1 to 20 carbon atoms, a cyclic compound having from 1 to 20 carbon atoms, an unsubstituted compound having from 1 to 20 carbon atoms, a substituted compound having from 1 to 20 carbon atoms, an aliphatic compound having from to 20 carbon atoms, an unsubstituted aromatic compound having from 6 to 10 carbon atoms, or a substituted aromatic compound having from 6 to 10 carbon atoms, hydrazine, dimethyl carbonate, and mixtures thereof.

9. The process according to claim 1, wherein the distillation is carried out at a pressure ranging from 0.1 to 30 mbar.

10. The process according to claim 1, wherein the second solvent is selected from the group consisting of benzene, toluene, xylene, chlorobenzene, and mixtures thereof.

11. A process for preparing a methyl carbazate from hydrazine and dimethyl carbonate comprising:

(A) simultaneously metering hydrazine and dimethyl carbonate into an initially introduced first solvent at a temperature ranging from −20 to +30° C., (B) distilling off the solvent and low-boiling components under reduced pressure, and (C) adding a second solvent to crude methyl carbazate present and passing a as through crude methyl carbazate resent.

12. The process according to claim 11, wherein the hydrazine and the dimethyl carbonate are present at a molar ratio ranging from 0.9 to 1.1:1.

13. The process according to claim 11, wherein the first solvent is water or an organic solvent is selected from the group consisting of a straight-chain compound having from 1 to 20 carbon atoms, a branched compound having from 1 to 20 carbon atoms, a cyclic compound having from 1 to 20 carbon atoms, an unsubstituted compound having from 1 to 20 carbon atoms, a substituted aliphatic compound having from 1 to 20 carbon atoms, an unsubstituted aromatic compound having from 6 to 10 carbon atoms, an substituted aromatic compound having from 6 to 10 carbon atoms, and mixtures thereof.

14. The process of claim 13, wherein the hydrazine or the dimethyl carbonate is metered in at a molar excess of not greater than 20%, based on the other reactant, per time unit.

15. The process according to claim 11, wherein the first solvent is a straight-chain or a branched aliphatic alcohol having 1 to 8 carbon atoms.

16. The process according to claim 11, wherein the simultaneous metering is carried out so that the hydrazine or the dimethyl carbonate is metered in at a molar excess that is not more than 20%, based on the other reactant, per time unit.

17. The process according to claim 11, wherein the process further comprises a post-reaction time period in which stirring is carried out at a temperature ranging rom +30 to +60° C. from 30 to 300 minutes after the metering.

18. The process according to claim 11, wherein the second solvent is an organic solvent selected from the group consisting of a straight-chain compound having from 1 to 20 carbon atoms, a branched compound having from 1 to 20 carbon atoms, a cyclic compound having from 1 to 20 carbon atoms, an unsubstituted compound having from 1 to 20 carbon atoms, a substituted compound having from 1 to 20 carbon atoms, an aliphatic compound having from 1 to 20 carbon atoms, an unsubstituted aromatic compound having from 6 to 10 carbon atoms, or a substituted aromatic compound having from 6 to 10 carbon atoms, hydrazine, dimethyl carbonate, and mixtures thereof.

19. The process according to claim 11, wherein distillation is carried out at a pressure ranging from 0.1 to 30 mbar.

20. The process according to claim 11, wherein the second solvent is selected from the group consisting of benzene, toluene, xylene, chlorobenzene, and mixtures thereof.

21. The process according to claim 11, wherein the process further comprises passing nitrogen, air, oxygen or a noble gas, or mixtures thereof through crude methyl carbazate at a temperature ranging from 75 to 120° C.

* * * * *